(12) United States Patent
Metteer

(10) Patent No.: US 8,845,782 B2
(45) Date of Patent: *Sep. 30, 2014

(54) MODULAR DUCTWORK DECONTAMINATION ASSEMBLY

(71) Applicant: Karen Metteer, Fresno, CA (US)

(72) Inventor: Karen Metteer, Fresno, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,989

(22) Filed: Mar. 5, 2013

(65) Prior Publication Data

US 2013/0183214 A1   Jul. 18, 2013

Related U.S. Application Data

(63) Continuation-in-part of application No. 12/819,848, filed on Jun. 21, 2010, now Pat. No. 8,388,731, which is a continuation-in-part of application No. 12/017,671, filed on Jan. 22, 2008, now Pat. No. 7,740,686.

(60) Provisional application No. 60/885,980, filed on Jan. 22, 2007.

(51) Int. Cl.
| | | |
|---|---|---|
| B03C 3/14 | (2006.01) | |
| B03C 3/16 | (2006.01) | |
| A61L 9/015 | (2006.01) | |
| A61L 9/20 | (2006.01) | |
| A61L 9/02 | (2006.01) | |
| B01D 53/75 | (2006.01) | |
| B01D 53/72 | (2006.01) | |
| F24F 3/16 | (2006.01) | |
| C02F 1/78 | (2006.01) | |
| B01D 53/32 | (2006.01) | |

(52) U.S. Cl.
CPC ........... *A61L 9/015* (2013.01); *C02F 2201/782* (2013.01); *B01D 2257/91* (2013.01); *A61L 2209/212* (2013.01); *B01D 2251/104* (2013.01); *F24F 2003/1635* (2013.01); *F24F 2003/1671* (2013.01); *C02F 1/78* (2013.01); F24F 3/166 (2013.01); *A61L 2209/16* (2013.01); *B01D 2257/90* (2013.01); *B01D 2257/708* (2013.01); *B01D 2257/106* (2013.01); *B01D 2259/804* (2013.01); *B01D 53/323* (2013.01); *C02F 2303/04* (2013.01); B01D 53/32 (2013.01); *A61L 9/20* (2013.01); *C02F 2307/14* (2013.01); *F24F 2003/1685* (2013.01); A61L 9/02 (2013.01); B01D 53/75 (2013.01); B01D 53/72 (2013.01); F24F 3/1603 (2013.01)

USPC ............. 95/2; 95/3; 95/63; 95/69; 95/70; 95/78; 95/16; 95/18; 95/19; 95/55; 95/57; 95/64; 95/74; 95/224; 422/24; 422/28; 422/123; 422/124; 422/186.07; 422/186.13

(58) Field of Classification Search
USPC ............ 95/2, 3, 58, 63, 69, 70, 78; 96/16, 18, 96/19, 52, 55, 57, 63, 64, 74, 94, 224; 422/24, 28, 123, 124, 186.07, 186.13
See application file for complete search history.

(56) References Cited

U.S. PATENT DOCUMENTS

| | | | |
|---|---|---|---|
| 3,804,942 A * | 4/1974 | Kato et al. ................. | 423/239.1 |
| 3,804,945 A | 4/1974 | Scott et al. | |

(Continued)

FOREIGN PATENT DOCUMENTS

GB          2036951         7/1980

OTHER PUBLICATIONS

Non-Final Rejection in U.S. Appl. No. 12/819,848 dated Jun. 6, 2012.

*Primary Examiner* — Duane Smith
*Assistant Examiner* — Sonji Turner
(74) *Attorney, Agent, or Firm* — McAndrews, Held & Malloy Ltd.

(57) ABSTRACT

A modular ductwork assembly decontaminates an air stream circulating within a heating, ventilation and air conditioning (HVAC) system. The assembly includes one or more of (a) an ionizing module for removing particulates from the air stream, (b) a sterilization module for neutralizing airborne pathogens present in the air stream, (c) an ozone treatment module for neutralizing pathogens or odoriferous or gaseous constituents or volatile organic compounds (VOCs) present in the air stream, optionally (d) baffles for slowing and disrupting the flow rate and promoting turbulence in the air stream traveling through the modules, optionally (e) a fan module for directing a treated air stream, optionally (f) an ozone sensor, optionally (g) a monitoring or ozone control means, and optionally (h) a means of delivering and repurposing generated ozone. Each of the modules is arranged substantially adjacent to at least one of the other modules.

26 Claims, 5 Drawing Sheets

(56) References Cited

U.S. PATENT DOCUMENTS

| | | |
|---|---|---|
| 3,844,741 A | 10/1974 | Dimitrik |
| 5,656,063 A | 8/1997 | Hsu |
| 5,667,563 A | 9/1997 | Silva |
| 5,993,738 A | 11/1999 | Goswani |
| 6,063,170 A | 5/2000 | Deibert |
| 6,375,714 B1 | 4/2002 | Rump et al. |
| 6,623,544 B1 | 9/2003 | Kaura |
| 7,740,686 B2 | 6/2010 | Metteer et al. |
| 8,388,731 B2 * | 3/2013 | Metteer ............... 95/3 |
| 2002/0144601 A1 | 10/2002 | Palestro et al. |
| 2003/0217641 A1 | 11/2003 | Palestro et al. |
| 2005/0150386 A1 | 7/2005 | Cheng |
| 2006/0201328 A1 | 9/2006 | Chiang |
| 2007/0022879 A1 | 2/2007 | Aiba |
| 2007/0227362 A1 | 10/2007 | Parker |
| 2008/0173178 A1 | 7/2008 | Metteer |
| 2010/0254852 A1 * | 10/2010 | Metteer ............... 422/4 |

* cited by examiner

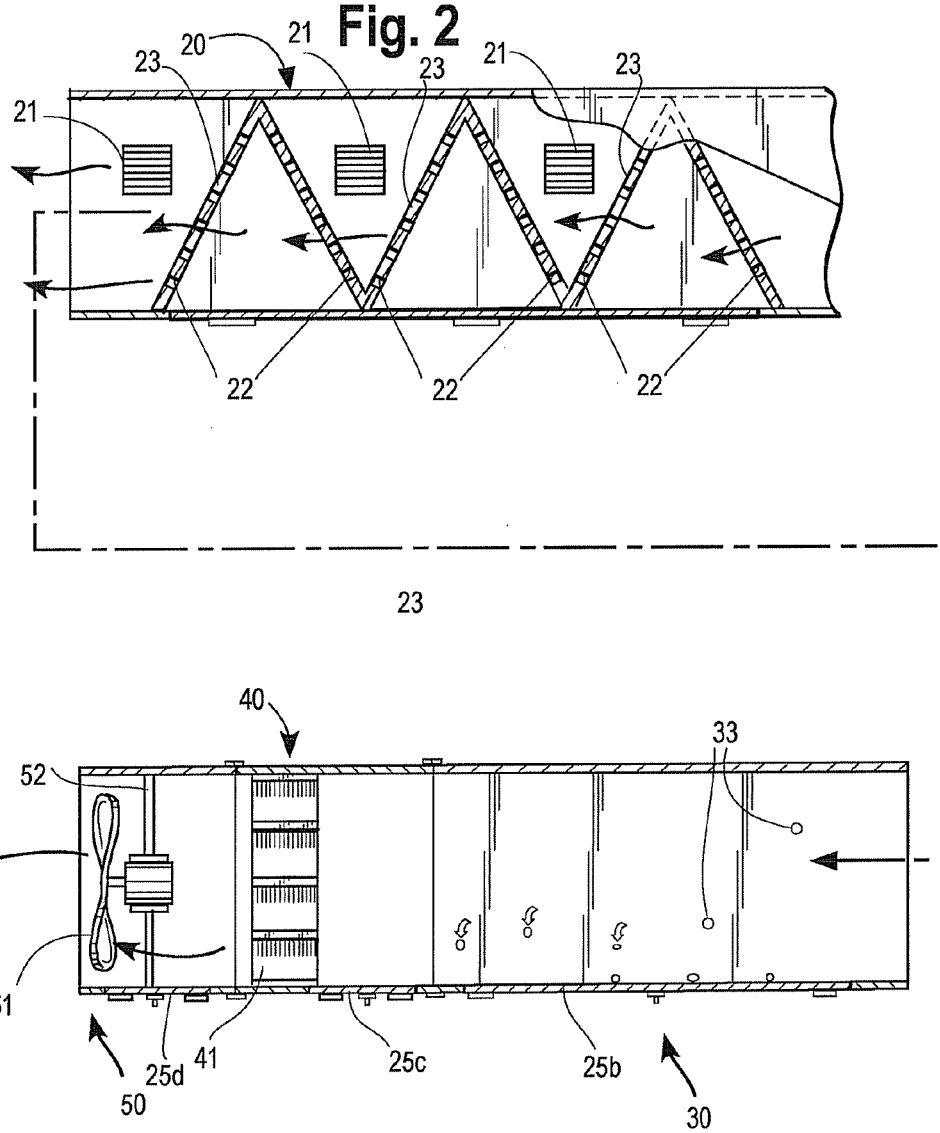

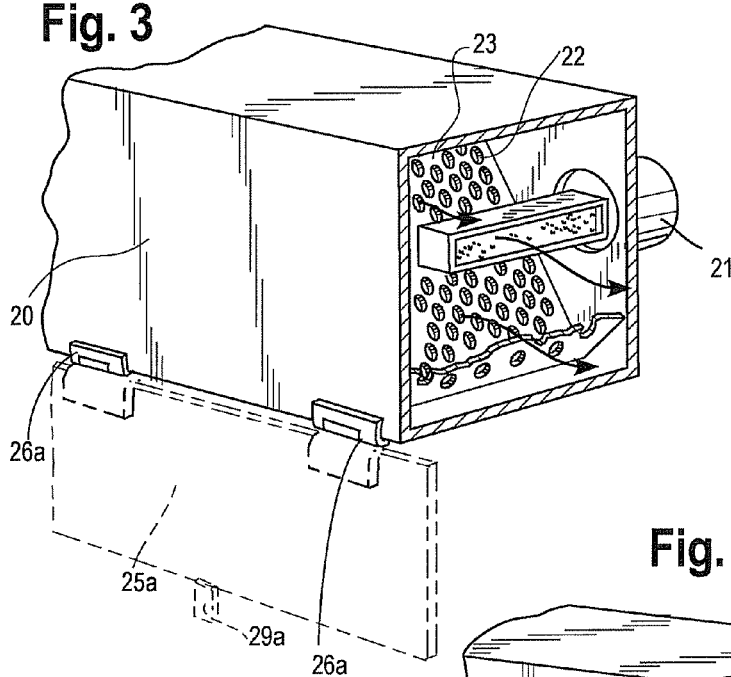
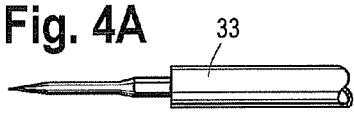
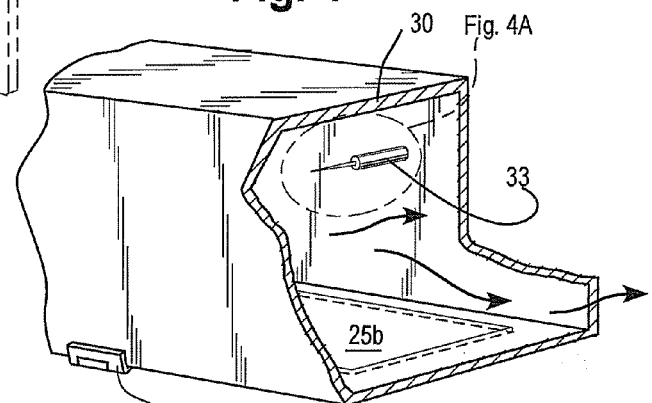
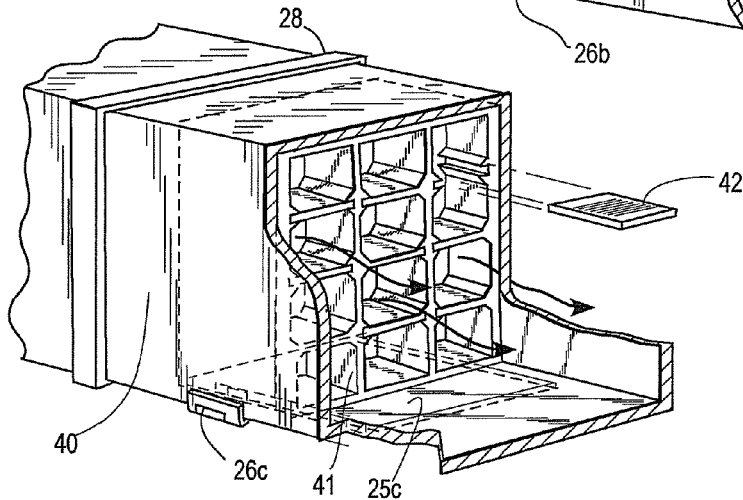

MODULAR DUCTWORK DECONTAMINATION ASSEMBLY

CROSS REFERENCE TO RELATED APPLICATION(S)

This application is a continuation-in-part of U.S. patent application Ser. No. 12/819,848, filed Jun. 21, 2010, now U.S. Pat. No. 8,388,731, which is a continuation-in-part of U.S. patent application Ser. No. 12/017,671, filed Jan. 22, 2008, now U.S. Pat. No. 7,740,686, which claims the benefit of the filing date under 35 U.S.C. 119(e) of Provisional U.S. Patent Application Ser. No. 60/885,980, filed Jan. 22, 2007, entitled "Modular Ductwork Decontamination Assembly." All of the foregoing applications are hereby incorporated by reference.

FIELD OF THE INVENTION

The present technology relates to heating, ventilation and air conditioning (HVAC) systems. In particular, the present technology relates to a modular ductwork assembly for decontaminating an air stream circulating within an HVAC system and for the repurposing of any ozone generated in the process.

BACKGROUND OF THE INVENTION

The present technique addresses the problem of reducing or eliminating contaminants, including particulate, dust, mold, mildew, odors, gases, bacteria, viruses and volatile organic compounds (VOCs), within the air stream of HVAC systems.

Several companies presently offer commercial ultraviolet (UV) probe lights that are configured to extend from the interior walls of HVAC ductwork to remediate indoor air contamination problems at discrete locations.

Configuring individual probes, ionizers and ozonators in HVAC ductwork on an as-needed basis is time-consuming and expensive. An electrician is hired to crawl alongside ductwork to install such ductwork components at recommended intervals (for example, every 15 feet (4.57 meters)), and then to install wiring to electrically connect each component to the building's main electrical system. UV probes are only capable of treating bacteria, ionizers only treat particulates and ozonators only treat odors. These components, by themselves, do not solve all of the air quality problems listed above, namely: mold, mildew, bacteria, viruses, VOCs, odors, gases and particulates at one location with one installation.

SUMMARY

The present technique is unique in that it provides modular ductwork units containing an array of air treatment technologies. The present modular ductwork decontaminating technique achieves this in a single location in a single installation with comparatively little effort, expense and maintenance. The present technique also provides a method of repurposing ozone that may be generated during decomtamination.

One or more of the shortcomings of prior, conventional air stream decontamination systems within HVAC ductwork is overcome by a modular ductwork assembly for decontaminating an air stream circulating within an HVAC system. The assembly may comprise: (a) a sterilization module for neutralizing airborne pathogens present in the air stream; (b) an ionizing module for removing particulates from the air stream; (c) an ozone treatment module for neutralizing odoriferous or gaseous constituents present in the air stream; (d) an ozone sensor; and (e) a method of diverting ozone into a water supply. Each of the modules may be arranged substantially adjacent to at least one of the other modules.

In one variation, a ductwork decontamination assembly further comprises a plurality of baffles for slowing and/or disrupting the flow rate and promoting turbulence in the air stream traveling through the modules.

In another variation, a ductwork decontamination assembly optionally includes a fan module for directing the air stream through the modules. At least one of the modules may comprise a latchable door for accessing the module interior.

In another variation, the ionizing module may comprise at least one ionizer, more preferably a plurality of ionizers. The at least one ionizer is capable of electrically charging particulates which may cause them to aggregate and fall on the module floor.

The sterilization module preferably comprises at least one lamp capable of directing ultraviolet radiation toward the air stream. The at least one lamp is capable of directing at least one of ultraviolet (UV) radiation, ultraviolet-C (UVC) and ultraviolet-X (UVX) radiation toward the air stream, thereby sterilizing microbes and halting reproduction.

The ozone treatment module may comprise at least one ozone generator, more preferably a plurality of ozone generators, which may be capable of converting gaseous molecules into elements of carbon, hydrogen and oxygen.

Remote ozone sensors may be interposed to monitor gaseous ozone levels. The ozone sensors may be selectively located in areas with increased probability of ozone dumping or in areas where ozone dumping would be most harmful, such as near sensitive cancer patients, small children, elderly, and etc. For example, the ozone sensor may be located between the ozone generator and the off-gas bleed valve, between the ozone generator and an ozone-destruct device, near any areas where ozone may be utilized, such as water sources, and etc.

Ozone concentration in the air may vary by height because ozone is about 50 percent heavier than air. Remote ozone sensors may be placed at about head height, for example, to sample ozone as breathed by humans. In hospitals, nursing homes, and schools, this height may require adjustment. For example, in hospitals, the height may be adjusted to the height of the reclined patient. In schools, this height may be adjusted to the height of a child. In nursing homes, the height may be adjusted to the height of an adult in a wheel chair, or reclining, and etc.

Remote ozone sensors may be connected to a control and/or alarm system, and/or any other means by which ozone levels may be monitored and/or controlled. Remote ozone sensors may communicate with control systems, which may be integrated within the sensor or may be separate. Control systems or the ozone sensor may communicate with and open and/or close vents that are located throughout the building.

The following example is illustrative and not limiting. An ozone monitor may be installed in an area between the generator and the off-gas bleed valve. The monitor may detect, for example, a break in the generator or in the tubing or piping connecting the generator to, for example, a water flow. The monitor may communicate the ozone accumulation to a control system which may close vents in the affected area to quickly and efficiently address the spread of ozone to sensitive areas, for example, areas of human contact. Alternatively or additionally, the control system may activate fans or ozone-destruct devices in affected areas to remediate ozone accumulation.

A method for decontaminating an air stream circulating within an HVAC system may further include a method of diverting ozone to further uses. For example, interposing of a least one turbine fan and/or device capable of suctioning air flow from within ozone module. The ozone module may be within and/or adjacent to ductwork assembly, and/or may be placed at any isolated location within the ductwork system as deemed appropriate for distribution at specific location(s). The suctioning device and/or fan may bring ozone produced by, for example, an ozonating module via a conveyance system to, for example, at least one designated water system for the purpose of disinfecting/decontaminating said water system. The conveyance system may be sealed.

Ozone carried from, for example, an ozonating module to water system may be discharged into water, for example, by any or all of percolation, by creating water turbulence under air pressure, a combination of these, and/or other possible methods whereby ozone is released. Optional remote ozone sensors may measure and/or control the ozone discharge into the water and may measure and/or control the ozone released by the water.

Ozonated water may then be made available in predetermined saturation levels to optionally chosen applications, such as surgical scrub, housekeeping disinfection, food preparation and storage, fungus and mold/mildew remediation, etc. Ozone released via outgassing from water may be captured and may be vented and/or converted by ozone-destruct technology, such as catalytic oxidation reactor.

The suctioning device and/or fan may additionally or alternatively bring ozone produced by ozonating module via a conveyance system to be used otherwise. For example, the ozone may be injected into soil under plastic for weed control; may be injected to clean and decontaminate irrigation lines; may be injected to clean and decontaminate sewer lines; to clean and disinfect building sites, ground water, well water, and/or septic systems.

The method for decontaminating an air stream and repurposing ozone generated therein may be particularly applicable to disaster sites, war sites, and other areas—such as poverty stricken regions—to allow an institution, such as an emergency health station, outpost hospital, school, nursing facility, or otherwise, to function, for example, with decreased incidence of nosocomial infection and inexpensively. As a non-limiting example, when regions are subjected to natural disasters, war, and poverty, it is common that the food and ground water are contaminated with waste. Often, areas of poverty and war depend on in-ground septic systems which can leach into nearby areas, such as farming and food production areas, causing increased illness. The method described herein may allow for the removal of air contaminants and the ozone generated may be repurposed to decontaminate and also remove ground and water contaminants.

A method for decontaminating an air stream circulating within an HVAC system may comprise: (a) interposing an ionizing module in the air stream for removing particulates therefrom; (b) interposing a sterilization module in the air stream for neutralizing airborne pathogens present therein; and (c) interposing an ozone treatment module in the air stream for neutralizing odoriferous or gaseous constituents present therein; (d) interposing at least one remote ozone sensor; (e) interposing at least one alarm means; (f) interposing at least one control means; (g) interposing a method of delivering and repurposing generated ozone. Each of the modules is arranged substantially adjacent to at least one of the other modules.

The modular assembly may be capable of remediating contaminated indoor air streams in a single installation and with, for example, a single 110 VAC (60 Hz) electrical outlet.

BRIEF DESCRIPTION

FIG. 2 is a side sectional view of portions of the extendable modular ductwork decontamination assembly illustrated in FIG. 1.

FIG. 3 is a perspective view, partially in section, of a portion of the modular ductwork decontamination assembly illustrated in FIG. 1, which incorporates baffles for disrupting an air stream traveling through the modules and an ultraviolet/ultraviolet-C/ultraviolet-X (UV/UVC/UVX) sterilizing probe. A corresponding access door is shown in open position.

FIG. 4 is a perspective view, partially in section, of a portion of the present modular ductwork decontamination assembly, showing the mounting of an ionizer, with the corresponding access door in the closed position.

FIG. 4a is an enlarged side view of an ionizer employed in the present modular decontamination assembly.

FIG. 5 is a perspective view, partially in section, of a portion of the present modular ductwork decontamination assembly, showing the componentry of the ozone treatment module. A corresponding access door is shown in closed position.

DETAILED DESCRIPTION

Ozone has been demonstrated to be an effective reagent to reduce the numbers of microbes contaminating food surfaces. It has been used to treat drinking water and irrigation systems. This disinfectant is a powerful oxidizing agent that has recently been given GRAS (Generally Recognized As Safe) status for use in food processing. Since it readily decomposes into oxygen, there are no chemical residues that could contaminate the food product or the environment.

The growing extent of microbial contamination of food and changing demographics has led to increasing frequency of food borne illness. Significant amounts of pathogens including *Escherichia coli* 0157:H7 and *Salmonella typhimurium*, cross-contaminate beef carcasses throughout processing and can further contaminate ground beef or processed beef products.

Ozone is used for water treatment because it oxidizes or disinfects many components that impact water quality. It will oxidize iron and manganese which precipitate as ferric and manganese hydroxides. It partially oxidizes organic matter to forms that are more easily biodegradable. Ozone is also germicidal against many types of pathogenic organisms including viruses, bacteria and protozoa.

The ozone may oxidize any materials that a grower injects into the irrigation lines at the same time as the ozone. For example, if growers inject fertilizer such as fish emulsion or other material into the irrigation system, ozone will oxidize the material. The extent may depend on the concentration of the added material, the concentration of the ozone and the contact time.

In water there are at least two modes of action by ozone, direct oxidation and oxidation by hydroxyl free radicals. Ozone, among other things, oxidizes organic matter, attacks bacterial membranes, disrupts enzymatic activity, disassociates viral capsids and attacks RNA.

Disinfection and chemical oxidation rates by ozone may be relatively independent of temperature. If recirculated irrigation water is treated with ozone, the excess ozone may be scrubbed to prevent release to the atmosphere and to protect workers from ozone exposure.

Figure 1:
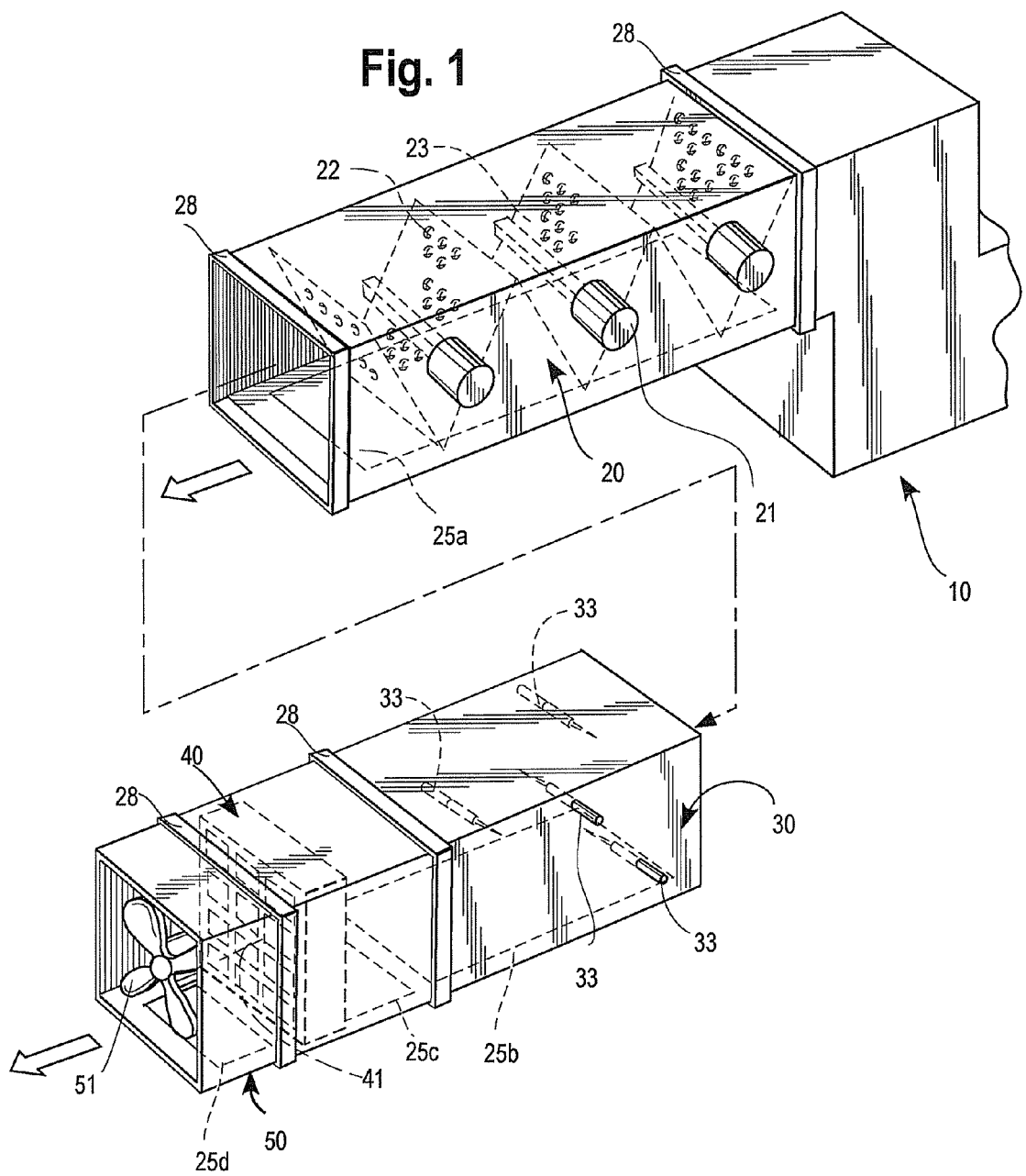
FIG. 1 is a perspective view of the present modular ductwork decontamination assembly, showing the interior components in hidden lines.

Turning first to FIG. 1, HVAC system 10 directs an air stream (depicted by a hollow, exiting arrow) through a ductwork system. Ductwork decontamination assembly 20, in regular 4 foot (1.22 m), 5 foot (1.52 m), 10 foot (3.04 m) or other customized lengths, can be variously shaped to satisfy treatment and design needs. Barriers/baffles 23, arranged according to size and shape of the ductwork housing, are intended to slow the incoming air stream flow from the upstream HVAC system. Perforations 22, arranged in various patterns and sizes, are intended to impart turbulence and thereby effectively mix the air stream flowing through the interior passageway of ductwork 20.

Optional modules are included in the ductwork. These optional modules can include a sterilization module, an ionizing module, an ozone treatment module and fan modules. The optional modules can further include one or more of remote ozone sensors, alarm means, control means, and means for delivering and repurposing potentially generated ozone. The sterilization module may neutralize airborne pathogens present in the air stream using any UV generating probe, including but not limited to one or more of an ultraviolet, ultraviolet-C, ultraviolet-X (UV/UVC/UVX) sterilizing probe.

The ionizing module may remove particulates from the air stream by charging the particulates which may cause them to aggregate and fall out of the air stream. The ozone treatment module may, among other things, neutralize odoriferous or gaseous constituents present in the air stream by, for example but not limited to, converting gaseous molecules into elements of carbon, hydrogen and oxygen. The modules can be ordered in various arrangements depending on the space available and the user's needs.

HVAC fittings 28 provide connection(s) between the upstream HVAC system and module fittings (and optionally other fittings), for the optional sterilization module(s), optional ionizing module(s), optional ozone treatment module(s), the remaining optional fan modules, and between other optional ductwork before, between or after the module(s).

One of the benefits of the current modular ductwork contamination system is that it is extendable and repeatable. This allows the user to customize a ductwork system to his or her particular needs. For example, in an environment where pathogens are a concern, such as a hospital, a food production center (e.g., a slaughter house, food packaging plant, etc.), nursing home, school, or military war injury unit, multiple sterilization modules could be used in order to further sterilize the air stream. In another example, multiple ozone treatment modules could be used for particularly odiferous or gaseous areas.

In one embodiment, the optional modules can be located close to the HVAC center. The air can then be treated at its source before going off to the other areas of the building. In some situations it will be desirable to put modules on each floor, so that the air is consistent throughout the building. As discussed above, certain modules could also be congregated where certain concerns exist, such as odor or gas problems, particulate problems and pathogen problems. The modules could also be located in different areas due to space constraints of the HVAC ductwork.

As shown in FIG. 1 the ionizing modules may be isolated from the sterilization modules and ozone treatment modules. This may prevent or limit particulate accumulation. When the particulate matter is charged by the ionizer it may aggregate and fall to the ground or walls of the module. This could become problematic if the sterilization probes or ozone generators were located in the same module because they could, assuming supplementary clearance or control methods are not employed, become covered in particulate matter. The probes or ozone generators might not function as efficiently unless cleaned often. Separating the ionizing modules from the other modules may avoid this complication.

FIG. 2 shows extendable modular ductwork decontamination assembly with optional arrangements of UV sterilization 20 and ionizer components 30 alternating from front to back and from back to front, with optional ozone generator module 40 and optional fan module 50. UV sterilization 20 includes all forms of UV sterilization, for example, but not limited to one or more of ultraviolet (UV) radiation, ultraviolet-C (UVC) and ultraviolet-X (UVX) radiation.

Ionizers 33 in ionization module 30 may affect particulate, causing aggregation and fallout on module floor as demonstrated by hollow arrows.

FIG. 3 shows the mounting of an ultraviolet lamp 21, as well as the location of hinge 26a of access door 25a. Ultraviolet (UV) and/or ultraviolet-C (UVC) and/or ultraviolet-X (UVX) and/or other type of ultraviolet lamp(s) 21, are arranged in various patterns, directions and/or positions between barriers/baffles 23 to sterilize the genetic material of airborne microorganisms and/or pathogens.

FIG. 4 ionizing module 30, contains mounted ionizer(s) 33, of potentially various types and/or sizes, arranged in various locations to, for example, electrostatically aggregate various forms of particulate matter, which may fall by static charge and gravity to the bottom of the ductwork housing. Access door 25b provides access to the interior of the ductwork module housing for cleaning and maintenance.

FIG. 5 shows one variation of componentry of ozone treatment module 40, and incldues a representative type of ozone generator 42. Module 40 is capable of housing various sizes and types of ozone generators. In this regard, ozone treatment module support frame 41 provides structural and attachment support for various sizes and types of ozone generators. Ozone generator(s) 42 generate sufficient ozone, preferably as regulated by remote control electrical switching or equivalent software, to remediate, for example but not limited to one or more of, various odors, gases, VOCs, pathogenic organisms, odor causing organisms, gas producing organisms, organic matter, viruses, and etc. Also shown is hinge 26c for access door 25c in closed position.

Figure 6:
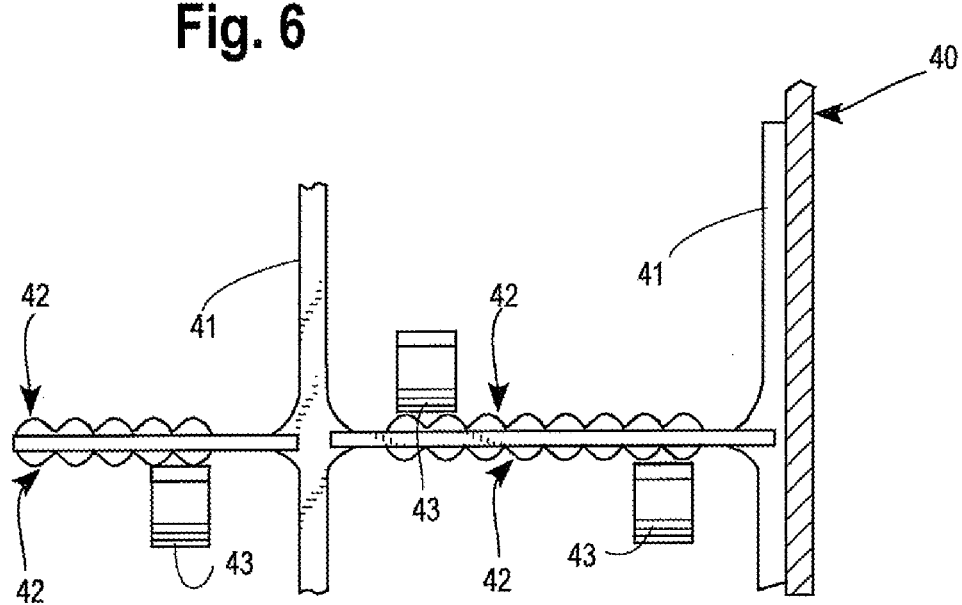
FIG. 6 is a front sectional view of the ozone treatment module of the modular ductwork decontamination assembly illustrated in FIG. 5.

FIG. 6 illustrates a side view embodiment of cathode/anode contacts 43 to provide electrical supply to ozone treatment generators 42 in ozonating module 40. Support structure 41 for ozonators 42 and electrical components 43 is fitted to module housing 40.

Figure 7:
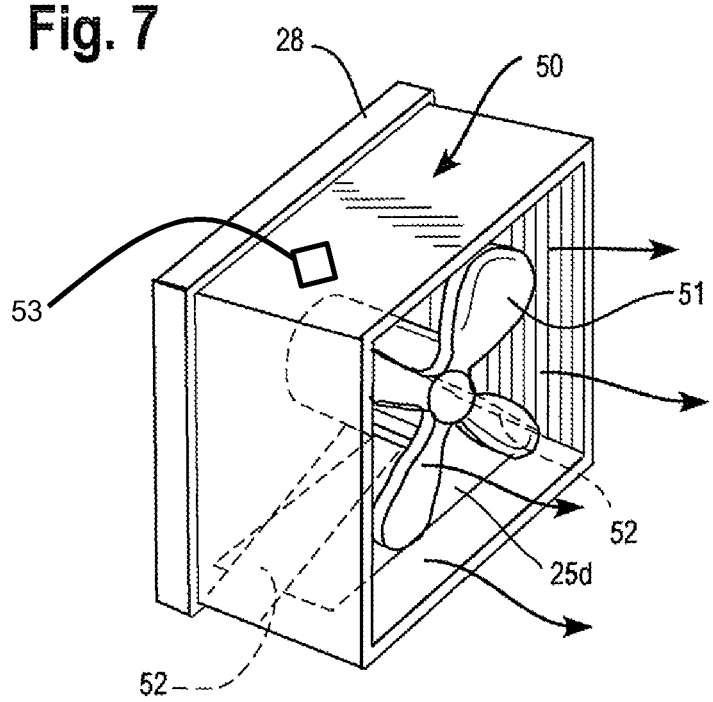
FIG. 7 is a perspective view of a portion of the present modular ductwork decontamination assembly, showing the fan module for directing the air stream through the HVAC ductwork.

FIG. 7 shows fan module 50, which includes attachment support(s) 52 and a fan 51 (could also be referred to optionally as a blower, vane or turbine). Fan module 50 is capable of housing various types and sizes of fans, blowers, vanes and/or turbines, which induce the treated air stream to flow at a rate (in cubic feet per minute (CFM) in English units or cubic meters per minute (CMM), 1.0 CFM being equal to 0.028 CMM) as required or desirable for the volume of recirculated air to be treated. Additionally shown is access door 25*d* in closed position. Additionally shown is ozone sensor 53

Figure 8:
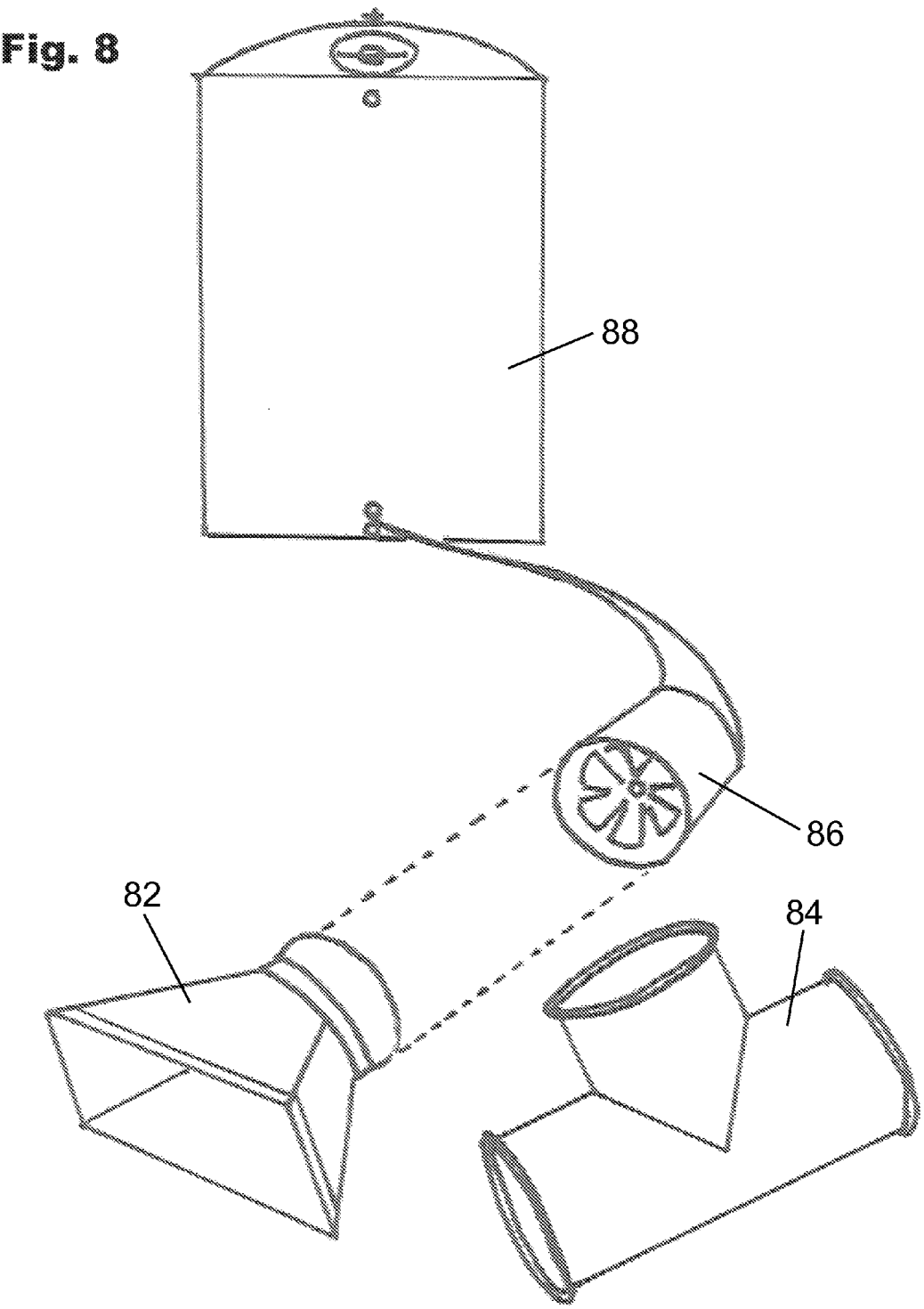
FIG. 8 is a perspective view of a portion of the present modular ductwork decontamination assembly showing a water decontamination module.

FIG. 8 shows a water decontamination module. The decontaminated air would exit FIG. 7 and optionally be fully or partially (depending on whether a "reducer" (82) or "ducting T branch" (84) is used) directed through an optional high velocity fan (86) to an optionally pressurized water tank (88). The decontaminated air with active ozone would optionally percolate and/or be pressurized throughout the water. The water would thus be potable, and, if highly ozonated, can be used as a disinfectant, such as in meat-packing industries.

FIG. 4*a* shows one type of ionizer 33 that is suitable for use in the present modular ductwork decontamination assembly. FIG. 5 shows the mounting of ozonator 42, with the corresponding access door 25*c* in the closed position. FIGS. 3, 4, 5 illustrate the location of access door hinges 26*a*, 26*b* and 26*c*, respectively. FIG. 3 demonstrates one module's access door latch 29*a* which secures access doors to the bottom of each module, thereby safely and securely shielding the exterior to ductwork assembly 20 from UV rays generated within the UV sterilization module. Door latch 29*a* also inhibits outside objects from entering the interior of ductwork assembly 20. Such secure latching can be applied to at least some modules.

As shown in FIGS. 1 & 2 (25*a*, 25*b*, 25*c*, 25*d*), FIG. 3 (25*a*), FIG. 4 (25*b*), FIG. 5 (25*c*), and FIG. 7 (25*d*), hinged, latchable doors provide access for cleaning and maintenance of the ductwork modules' interior surfaces as well as protection.

Note that the modules of the present extendable ductwork decontamination assembly can be arranged in various sequences to customize air treatment in multiple areas with unique, individual treatment concerns. In this regard, the assembly could be optionally configured as follows: (1) additional ozone generators can be included, for example, for high odor or gas, VOC spaces, or high pathogen spaces; (2) additional ionizers could be included, for example, for heavy particulate spaces; (3) additional UV sterilization means, for example, but not limited to one or more of UV, UVC, UVX or optional UV lamps could be included, for example, in bacteria-, virus- and mold-infested spaces; (4) additional fans could be included, for example, for more expansive spaces requiring higher air stream flow rates to reach at least a portion of the space to be treated; (5) additional baffles with various types and sizes of perforations could be incorporated, for example, to slow and disrupt the flow rate and promote turbulence in heavily contaminated air streams; (6) remote ozone sensors placed at various heights and locations could be incorporated, for example, to identify ozone accumulations, and possibly communicate information to an alarm and/or control means (which may be separate or integrated); (7) one or more alarm means may be placed in communication with ozone sensors, for example, to alert individuals to ozone accumulations or to communicate with a control means (which may be separate or integrated); (8) at least one control means may be placed in communication with ozone sensors, for example, to control the opening or closing of vents and or activation of ozone-depletion or ozone-repurposing methods; (g) a means of delivering and repurposing generated ozone, for example, for sterilizing food surfaces, decontaminating water, or otherwise.

Remote ozone sensors may be interposed to monitor gaseous ozone levels. The ozone sensors may be selectively located in areas with increased probability of ozone dumping or in areas where ozone dumping would be most harmful, such as near sensitive cancer patients, small children, elderly, and etc. For example, the ozone sensor may be located between the ozone generator and the off-gas bleed valve, between the ozone generator and an ozone-destruct device, near any areas where ozone may be utilized, such as water sources, and etc.

Ozone concentration in the air may vary by height because ozone is about 50 percent heavier than air. Remote ozone sensors may be placed at about head height, for example, to sample ozone as breathed by humans. In hospitals, nursing homes, and schools, this height may require adjustment. For example, in hospitals, the height may be adjusted to the height of the reclined patient. In schools, this height may be adjusted to the height of a child. In nursing homes, the height may be adjusted to the height of an adult in a wheel chair, reclining, and etc.

Remote ozone sensors may be connected to a control and/or alarm system, and/or any other means by which ozone levels may be monitored and/or controlled. Remote ozone sensors may communicate with control systems, which may be integrated within the sensor or may be separate. Control systems or the ozone sensor may communicate with and open and/or close vents that are located throughout the building.

The following example is illustrative and not limiting. An ozone monitor may be installed in an area between the generator and the off-gas bleed valve. The monitor may detect, for example, a break in the generator or in the tubing or piping connecting the generator to, for example, a water flow. The monitor may communicate the ozone accumulation to a control system which may close vents in the affected area to quickly and efficiently address the spread of ozone to sensitive areas, for example, areas of human contact. Alternatively or additionally, the control system may activate fans or ozone-destruct devices in affected areas to remediate ozone accumulation.

A method for decontaminating an air stream circulating within an HVAC system may further include a method of diverting ozone to further uses. For example, interposing of a least one turbine fan and/or device capable of suctioning air flow from within ozone module. The ozone module may be within and/or adjacent to ductwork assembly, and/or may be placed at any isolated location within the ductwork system as deemed appropriate for distribution at specific location(s). The suctioning device and/or fan may bring ozone produced by ozonating module via a conveyance system to, for example, at least one designated water system for the purpose of disinfecting/decontaminating said water system. The conveyance system may be sealed.

Ozone carried from ozonating module to water system may be discharged into water, for example, by any or all of percolation, by creating water turbulence under air pressure, or other possible methods whereby ozone is released. Optional remote ozone sensors may optionally measure and/or control the ozone discharge into the water and optionally measure and/or control the ozone released by the water.

Ozonated water may then be made available in optionally predetermined saturation levels to optionally chosen applications, such as surgical scrub, housekeeping disinfection, food preparation and storage, fungus and mold/mildew remediation, etc. Ozone released via outgassing from water would optionally be captured and optionally vented and/or converted by ozone-destruct technology, such as catalytic oxidation reactor.

The suctioning device and/or fan may additionally or alternatively bring ozone produced by ozonating module via a conveyance system to be used otherwise. For example, the ozone may be injected into soil under plastic for weed control; may be injected to clean and decontaminate irrigation lines;

may be injected to clean and decontaminate sewer lines; to clean and disinfect building sites, ground water, well water, and/or septic systems.

The method for decontaminating an air stream and repurposing ozone generated therein may also be applicable to provide increased disease control, water, and air quality to institutions such as emergency health stations, outpost hospitals, schools, and nursing facilities located at disaster sites and war sites. As a non-limiting example, when regions are subjected to natural disasters, war, and poverty, it is common that the food and ground water are contaminated with waste. Often, areas of poverty and war depend on in-ground septic systems which can leach into nearby areas, such as farming and food production areas, causing increased illness. The method described herein may allow for the removal of air contaminants and the ozone generated may be repurposed to decontaminate and also remove ground and water contaminants.

Additionally or alternatively, ozone may be repurposed to aqueous ozone, which may also be used to cause significant reduction of pathogens from fresh cut vegetables and beef surfaces.

The present modular ductwork decontamination assembly can be installed in various configurations within an HVAC system outlet or as needed within the extended ductwork system to treat individual interior spaces. Maintenance, cleaning and parts replacement may occur at the modular component site only, and not along ductwork routes. Individual, sequential installations of various types of treatment units by an electrician may not be necessary. Probes, ionizers and ozonators may be routinely checked, cleaned or replaced at one time and at one location. This makes the present modular ductwork decontamination assembly efficient, timesaving and economical by comparison with current ductwork cleaning and maintenance methods. A single, modular assembly can be designed to treat an entire home or an entire floor of a building. This is a vast improvement over placing air cleaning units within individual interior spaces to be treated and hiring electricians to wire probes at regular intervals in an HVAC ductwork system.

One or more of the following results is achievable using the present modular ductwork decontamination assembly: (1) particulate is removed from the air without the use of expensive, high-maintenance filters. Particles are electronically charged to clump and fall by gravity onto the ductwork access door. (2) harmful microorganisms are rendered reproductively sterile through DNA alteration provided by UV sterilization, such as but not limited to one or more of UV, UVC, UVX light and/or ozone generation. (3) VOCs, odors, gases and/or pathogenic organisms including but not limited to viruses, bacteria, and protozoa, may be reduced by, for example, altering the molecular structure of the gaseous elements and converting these compounds into non-volatile elements, oxidizing organic matter, attacking bacterial membranes, disrupting enzymatic activity, disassociating viral capsids, attacking RNA, and otherwise. (4) ozone repurposed for the decontamination of water supplies, irrigation systems, septic and sewer systems, food preparation surfaces, and otherwise.

The present modular ductwork decontamination assembly has at least one or more of the following advantages over prior, conventional systems: (a) all treatment activity preferably occurs in one modular portion of the HVAC ductwork system rather than at variously scattered and individually located application modes. (b) all cleaning and maintenance takes place via the easy-access door(s) at the bottom of each ductwork module, which may be in one location. (c) probes are self-cleaning; ozonator plates and ionizers are readily cleaned and/or replaced, for example, via easy-access doors; parts are replaceable components. (d) installation, cleaning and maintenance of the present modular ductwork decontamination assembly is more economical than for scattered and individually located filter units, probes, ionizers and ozonators. Additionally, the present assembly does not employ expensive, high-efficiency particulate air (HEPA) type filters that must be cleaned and/or replaced. (e) modular air-purifying ductwork can be designed by the building architect into the HVAC system as an integral part of the construction. Airflow treatment and delivery can be predetermined for each ductwork module. Thus the time expenditure and difficulty of collecting and calibrating various types of flow rate (CFM/CMM) information for various kinds of air treatment systems is unnecessary. Each ductwork module's CFM/CMM treatment effectiveness is predetermined and controlled remotely according to the owner's preference. (f) internal arrangement and numbers of the sterilizing ductwork module's various sizes, baffles, UV probes, ionizers, and ozonators as well as types and sizes of perforations and fans can be designed to suit the treated area's specific size, air quality issues, and temperature range. (g) repurposing of ozone to further decontaminate the area by decontaminating water, food surfaces, irrigation, sewer systems, and etc.

While particular elements, embodiments and applications of the present invention have been shown and described, it will be understood, of course, that the invention is not limited thereto since modifications may be made by those skilled in the art without departing from the spirit and scope of the present disclosure, particularly in light of the foregoing teachings.

What is claimed is:

1. A modular ductwork assembly for decontaminating an air stream circulating within an HVAC system, the assembly comprising:
   (a) at least one ionizing module for removing particulates from said air stream;
   (b) at least one sterilization module for neutralizing airborne pathogens present in said air stream; and
   (c) at least one ozone treatment module for neutralizing odoriferous or gaseous constituents present in said air stream,
   wherein each of said modules is arranged substantially adjacent to at least one of the other modules.

2. The ductwork decontamination assembly of claim 1, further comprising a plurality of baffles for disrupting the air stream traveling through the modules.

3. The ductwork decontamination assembly of claim 1 further comprising at least one ozone sensor for monitoring gaseous ozone levels.

4. The ductwork decontamination assembly of claim 1, further comprising a control module by which ozone levels may be controlled.

5. The ductwork decontamination assembly of claim 1, further comprising an alarm by which ozone levels may be monitored.

6. The ductwork decontamination assembly of claim 1, further comprising a conveyance means to bring ozone produced by the ozonating module to at least one designated water system for the purpose of decontaminating the water system.

7. The ductwork decontamination assembly of claim 1, further comprising a fan module for directing said air stream through said modules.

8. The ductwork decontamination assembly of claim 1, wherein at least one of said modules comprises a latchable door for accessing said module interior.

9. The ductwork decontamination assembly of claim 1, wherein said ionizing module comprises at least one ionizer.

10. The ductwork decontamination assembly of claim 1, wherein said sterilization module comprises at least one lamp capable of directing ultraviolet radiation toward said air stream.

11. The ductwork decontamination assembly of claim 10, wherein said at least one lamp is capable of directing at least one of ultraviolet radiation, ultraviolet-C, ultraviolet-X, or other safe form of sterilizing light toward said air stream.

12. The ductwork decontamination assembly of claim 1, wherein said ozone treatment module comprises at least one ozone generator.

13. The ductwork decontamination assembly of claim 8, wherein said at least one ozone generator comprises a plurality of ozone generators.

14. The ductwork decontamination assembly of claim 1, wherein the ionizing module is separated from the sterilization module and the ozone treatment module.

15. A method for decontaminating an air stream circulating within an HVAC system, the method comprising:
(a) interposing at least one ionizing module in said air stream for removing particulates therefrom;
(b) interposing at least one sterilization module in said air stream for neutralizing airborne pathogens present therein; and
(c) interposing at least one ozone treatment module in said air stream for neutralizing odoriferous or gaseous constituents or volatile organic compounds present therein, wherein each of said modules is arranged substantially adjacent to at least one of the other modules.

16. The method of decontaminating an air stream circulating within an HVAC system of claim 15, further comprising interposing at least one ozone sensor in a remote location for at least one of monitoring or controlling ozone levels.

17. The method for decontaminating an air stream circulating within an HVAC system of claim 15, further comprising disrupting the air stream through the modules using a plurality of baffles.

18. The method for decontaminating an air stream circulating within an HVAC system of claim 15, further comprising directing said air stream through said modules using a fan module.

19. The method for decontaminating an air stream circulating within an HVAC system of claim 15, wherein said ionizing module comprises at least one ionizer.

20. The method for decontaminating an air stream circulating within an HVAC system of claim 15, wherein said sterilization module comprises at least one lamp capable of directing ultraviolet radiation toward said air stream.

21. The method for decontaminating an air stream circulating within an HVAC system of claim 20, wherein said at least one lamp is capable of directing at least one of ultraviolet radiation, ultraviolet-C, ultraviolet-X, or other safe form of sterilizing light toward said air stream.

22. The method for decontaminating an air stream circulating within an HVAC system of claim 15, wherein said ozone treatment module comprises at least one ozone generator.

23. The method for decontaminating an air stream circulating within an HVAC system of claim 22, wherein said at least one ozone generator comprises a plurality of ozone generators.

24. The method for decontaminating an air stream circulating within an HVAC system of claim 15, wherein the ionizing module is separated from the sterilization module and the ozone treatment module.

25. A method of customizing a ductwork assembly for decontaminating an air stream circulating within an HVAC system, the method comprising:
(a) assessing a problem from the group comprising pathogen problems, odor or gas problems, and particulate problems;
(b) interposing at least one ionizing module in said air stream where a particulate problem is assessed;
(c) interposing at least one sterilization module in said air stream where a pathogen problem is assessed; and
(d) interposing at least one ozone treatment module in said air stream where an odor or gas problem is assessed, wherein each of said modules is arranged substantially adjacent to at least one of the other modules.

26. The method of customizing a ductwork assembly for decontaminating an air stream circulating within an HVAC system of claim 25 further comprising (e) interposing at least one ozone sensor at a remote location; and (f) interposing at least one control means communicating with the ozone sensor.

* * * * *